United States Patent
Kawagishi et al.

(10) Patent No.: US 10,726,344 B2
(45) Date of Patent: Jul. 28, 2020

(54) DIAGNOSIS SUPPORT APPARATUS AND METHOD OF CONTROLLING THE SAME

(71) Applicant: CANON KABUSHIKI KAISHA, Tokyo (JP)

(72) Inventors: Masami Kawagishi, Kyoto (JP); Kiyohide Satoh, Kawasaki (JP); Yoshio Iizuka, Kyoto (JP); Takeshi Kubo, Kyoto (JP); Masahiro Yakami, Kyoto (JP); Koji Fujimoto, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 408 days.

(21) Appl. No.: 15/647,146

(22) Filed: Jul. 11, 2017

(65) Prior Publication Data

US 2017/0308661 A1 Oct. 26, 2017

Related U.S. Application Data

(63) Continuation of application No. 14/378,311, filed as application No. PCT/JP2013/052119 on Jan. 24, 2013, now Pat. No. 9,734,300.

(30) Foreign Application Priority Data

Feb. 14, 2012 (JP) ................................ 2012-029835

(51) Int. Cl.
*G06N 5/04* (2006.01)
*G06Q 50/22* (2018.01)
*A61B 5/00* (2006.01)
*A61B 6/00* (2006.01)
*G16H 50/20* (2018.01)
(Continued)

(52) U.S. Cl.
CPC ............... *G06N 5/04* (2013.01); *A61B 5/743* (2013.01); *A61B 6/461* (2013.01); *A61B 6/463* (2013.01); *G06Q 50/22* (2013.01); *G16H 50/20* (2018.01); *A61B 5/055* (2013.01); *A61B 6/032* (2013.01); *A61B 6/50* (2013.01)

(58) Field of Classification Search
USPC .......................................................... 706/12
See application file for complete search history.

(56) References Cited

U.S. PATENT DOCUMENTS 9,519,866 B2 * 12/2016 Kawagishi ............. G06N 7/005
9,715,657 B2 *  7/2017 Kawagishi ............... G06N 5/04
(Continued)

OTHER PUBLICATIONS

Elsevier Knowledge-Based Systems 14 (2001) pp. 327-335, Certainty-factor-like structures in Bayesian belief networks, P.J.F. Lucas Department of Computing Science, University of Aberdeen, Aberdeen UK.*

*Primary Examiner* — Michael B Holmes
(74) *Attorney, Agent, or Firm* — Canon U.S.A., Inc., IP Division

(57) ABSTRACT

A diagnosis support apparatus which supports diagnosis based on information associated with a diagnosis name in advance is provided. In the diagnosis support apparatus, an acquisition unit acquires the diagnosis name set by a user. A providing unit provides negative information for the diagnosis name set by the user based on the information. With the above arrangement, the diagnosis support apparatus selects and presents information influencing the diagnosis name expected by the user, thereby efficiently presenting information required by the user.

4 Claims, 7 Drawing Sheets

(51) Int. Cl.
*A61B 6/03* (2006.01)
*A61B 5/055* (2006.01)

(56) References Cited

U.S. PATENT DOCUMENTS

| | | | | |
|---|---|---|---|---|
| 9,734,299 B2* | 8/2017 | Yakami | ................. | G16H 50/20 |
| 9,734,300 B2* | 8/2017 | Kawagishi | ............ | A61B 5/743 |
| 9,808,213 B2* | 11/2017 | Endo | ..................... | A61B 6/466 |
| 9,916,425 B2* | 3/2018 | Kawagishi | ............ | G16H 50/20 |
| 9,940,438 B2* | 4/2018 | Kawagishi | ............ | G16H 50/70 |
| 9,940,715 B2* | 4/2018 | Fujimoto | ............. | G06F 19/321 |
| 10,049,445 B2* | 8/2018 | Nakano | ................. | G16H 30/40 |
| 10,181,187 B2* | 1/2019 | Kubo | ................... | G06T 7/0012 |
| 10,282,671 B2* | 5/2019 | Kawagishi | .............. | G06N 5/02 |
| 10,290,096 B2* | 5/2019 | Kawagishi | ........... | G06T 7/0012 |
| 10,497,118 B2* | 12/2019 | Nakano | ............... | G06T 7/0012 |
| 2009/0080732 A1* | 3/2009 | Zhou | ..................... | G06Q 50/22 |
| | | | | 382/128 |

* cited by examiner

FIG. 7

| j | $I_j$ (FINDING NAME) | jk | $S_{jk}$ (STATE NAME) |
|---|---|---|---|
| 1 | SHAPE | 11 | SPHERICAL |
| | | 12 | LOBULATED |
| | | 13 | IRREGULAR |
| 2 | LOBATION | 21 | STRONG |
| | | 22 | INTERMEDIATE |
| | | 23 | WEAK |
| | | 24 | NONE |
| 3 | RADIAL | 31 | STRONG |
| | | 32 | INTERMEDIATE |
| | | 33 | WEAK |
| | | 34 | NONE |
| ... | | | |
| n | ENGULFMENT (BLOOD VESSEL) | n1 | PRESENT |
| | | n2 | SUSPICIOUS |
| | | n3 | NONE |

DIAGNOSIS SUPPORT APPARATUS AND METHOD OF CONTROLLING THE SAME

CROSS-REFERENCE TO RELATED APPLICATIONS

This application is a Continuation of U.S. patent application Ser. No. 14/378311, filed Aug. 12, 2014, now U.S. Pat. No. 9,734,300, Date-Issued Aug. 15, 2017, which is a U.S. national stage application of International Patent Application No. PCT/JP2013/052119 with international filing date Jan. 24, 2013, and which claims foreign priority benefit of Japanese Patent Application No. 2012-029835, filed Feb. 14, 2012, all of which are hereby incorporated by reference herein in their entirety.

TECHNICAL FIELD

The present invention relates to a diagnosis support apparatus and, more particularly, to a diagnosis support apparatus which provides information for supporting medical diagnosis.

BACKGROUND ART

In the medical field, a doctor displays the medical images obtained by imaging a patient on a monitor, interprets the medical images displayed on the monitor, and observes the state of a morbid portion and temporal changes in it. Apparatuses which generate this type of medical images include, for example, an X-ray CT (Computed Tomography) apparatus, MRI (Magnetic Resonance Imaging) apparatus, and ultrasonic apparatus. Each diagnosis (image diagnosis) using these medical images can be divided into the step of finding an abnormal shadow or the like from the medical images as diagnosis targets and obtaining the characteristics of the shadow, and the step of performing differential diagnosis to identify the shadow.

Conventionally, there has been developed a medical diagnosis support apparatus which infers the identification of an abnormal shadow by using the characteristics (interpretation findings) of the shadow as input information and presents the resultant information to support differential diagnosis by doctors. For example, there has been proposed an apparatus which calculates the probability of a given shadow in a chest X-ray CT image being a malignant tumor and the probability of the shadow being a benign tumor and presents the resultant information. In general, the following is a proper procedure when using such an apparatus in an actual clinical site. First of all, the doctor performs differential diagnosis. The doctor then refers to the inference result output from the medical diagnosis support apparatus as reference information.

In this case, if the medical diagnosis support apparatus presents reference information (inference result) without any explanation, the doctor cannot determine the reliability of the reference information. Attempts have therefore been made to present information for helping the doctor to determine whether reference information is reliable, by presenting information (ground of an inference) used for the derivation of the reference information. Presenting information for determination concerning reference information can improve the degree of understanding of the doctor concerning the presented reference information. This can be expected to improve the degree of confidence of the diagnosis made by the doctor by himself/herself.

For example, Japanese Patent Laid-Open No. 2010-200840 has disclosed a technique of presenting negative information and positive information concerning the inference result obtained by an apparatus based on information which has been input (to be referred to as "already input information" hereinafter). This technique presents information concerning a diagnosis name (to be referred to as "estimated diagnosis name" hereinafter) exhibiting a highest inference probability (possibility) among inference results. Japanese Patent Laid-Open No. 2010-200840 has also disclosed a technique of presenting negative information and positive information concerning each of possible diagnosis names. This technique calculates the negation degree or affirmation degree of each piece of already input information concerning each estimated diagnosis name or each possible diagnosis name, and presents negative information and positive information. This makes it possible to present information influencing the derivation of the inference result from the apparatus based on the already input information.

If, however, there are many pieces of information which have not been input (to be referred to as "non-input information" hereinafter), the accuracy of inference by the medical diagnosis support apparatus is low. Attempts have therefore been made to obtain more reliable inference results by making an apparatus select non-input information necessary for inference and prompt the doctor to add the information. Prompting the doctor to check non-input information which might greatly influence an inference result is expected to provide the effect of improving the degree of confidence of diagnosis by the doctor himself/herself. In addition, it is expected to reduce diagnosis errors caused by interpretation oversights.

For example, Japanese Patent No. 3226400 has disclosed a technique of selecting and presenting non-input information to be noted from the inference result based on already input information and the inference result obtained when non-input information is added to already input information. This technique is designed to calculate the influence of each piece of non-input information with respect to the inference result and present non-input information exhibiting a high influence. As methods of calculating influences, there has been described a method focusing on the increased amount (decrease is not considered) of the inference probability of each estimated diagnosis name and a method focusing on the total sum of the change amounts of probabilities of possible diagnosis names. This makes it possible to present non-input information which greatly influences the inference result obtained by the apparatus based on already input information.

The technique disclosed in Japanese Patent Laid-Open No. 2010-200840 presents positive information and negative information concerning each estimated diagnosis name or each possible diagnosis name. The technique disclosed in Japanese Patent No. 3226400 presents non-input information in consideration of the change amount of probability of an estimated diagnosis name or the total sum of the change amounts of probabilities of the respective diagnosis names. This technique therefore may present no information influencing a specific diagnosis name other than an estimated diagnosis name in some cases, or present information concerning many diagnosis names other than information concerning the specific diagnosis name. For this reason, if the diagnosis name expected by the doctor differs from the estimated diagnosis name, there is a possibility that the apparatus may present no information required by the doctor or presents excessive amounts of information.

SUMMARY OF INVENTION

The present invention can efficiently present information required by doctors.

According to one aspect of the present invention, there is provided a diagnosis support apparatus which supports diagnosis based on information associated with a diagnosis name in advance, characterized by comprising: acquisition means for acquiring a diagnosis name set by a user; and providing means for providing negative information for the diagnosis name set by the user based on the information.

Further features of the present invention will become apparent from the following description of exemplary embodiments (with reference to the attached drawings).

BRIEF DESCRIPTION OF DRAWINGS

FIG. 7 is a view showing the correspondence relationship between interpretation findings and possible states in the first embodiment.

DESCRIPTION OF EMBODIMENTS

Various exemplary embodiments, features, and aspects of the invention will be described in detail below with reference to the drawings.

The embodiments of the present invention will be described in detail below with reference to the accompanying drawings. The present invention is not limited to the following embodiments, which are merely concrete examples advantageous to the implementation of the present invention. In addition, not all combinations of characteristic features described in the embodiments are essential to the solution of the problems in the present invention.

[First Embodiment]

A diagnosis support apparatus which supports diagnosis based on information associated with diagnosis names in advance will be described below. The medical diagnosis support apparatus according to the first embodiment acquires known medical information concerning a case as a diagnosis target as already input information, and supports diagnosis concerning the case.

The following is an example in which the medical diagnosis support apparatus acquires a plurality of interpretation findings concerning an abnormal shadow of the lung on a chest X-ray CT image as already input information, and presents diagnosis support information concerning the abnormal shadow. More specifically, this apparatus performs inference associated with the abnormality type (diagnosis name) of the abnormal shadow based on the already input information, and presents diagnosis support information based on the inference result. Obviously, an inference target is not limited to this, and the following diagnosis names, interpretation findings which can be input, and the like each are merely an example for explaining the steps in the processing performed by the medical diagnosis support apparatus.

Figure 1:
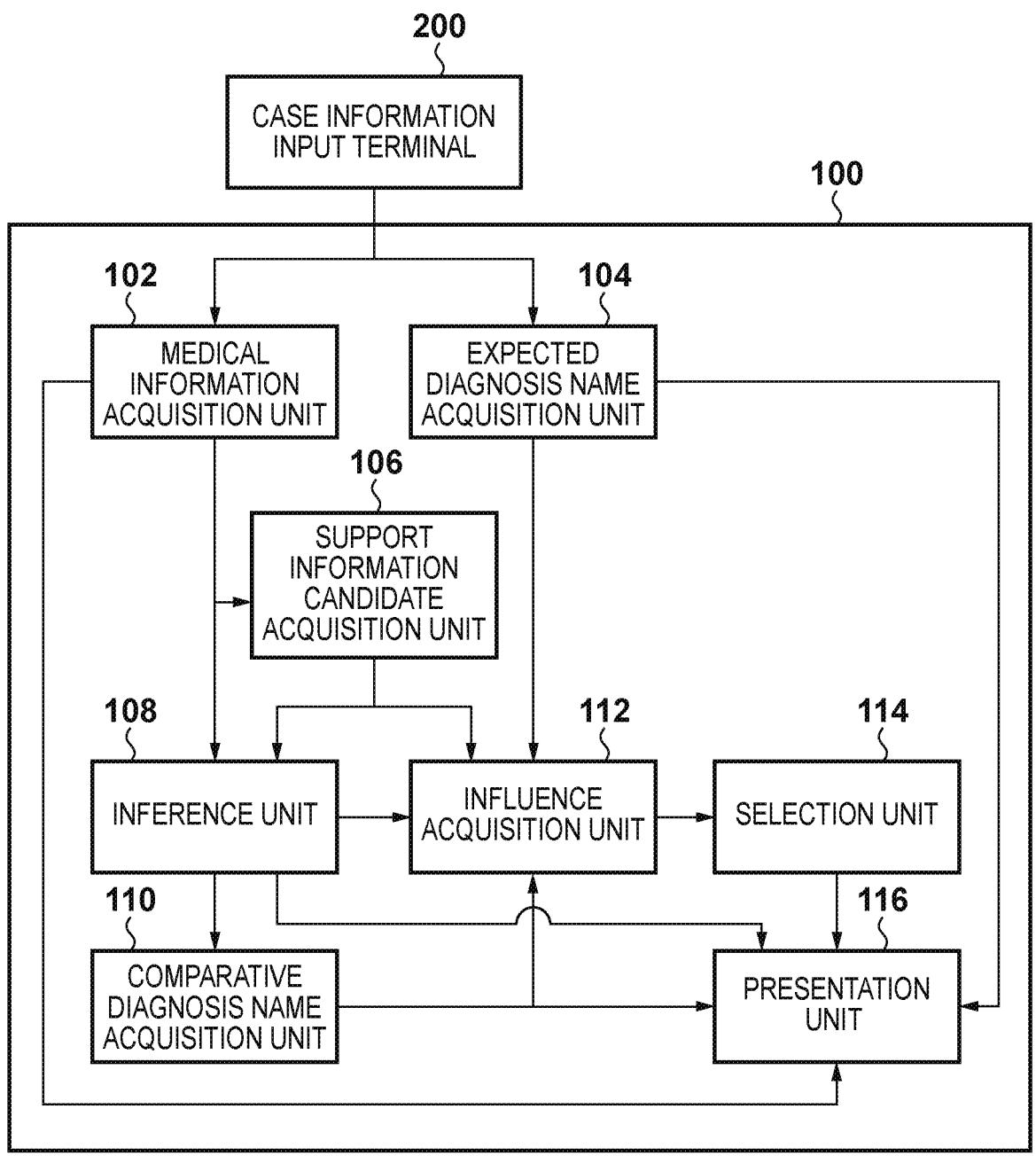
FIG. 1 is a block diagram showing the equipment configuration of a medical diagnosis support apparatus according to the first embodiment.

FIG. 1 is a block diagram showing the arrangement of the medical diagnosis support apparatus according to the first embodiment. As shown in FIG. 1, a medical diagnosis support apparatus 100 in this embodiment is connected to a case information input terminal 200.

The case information input terminal 200 acquires information (medical images, electronic chart information, and the like) associated with the abnormal shadow of the lung concerning a case as a diagnosis target from a server (not shown). The apparatus then displays a medical image on a monitor in a form that allows the user (doctor) to perform radiogram interpretation, and acquires the interpretation findings input by the user as already input information. The apparatus also acquires the diagnosis name input by the user as a result of radiogram interpretation as the diagnosis name expected by the user. In this embodiment, the user inputs the interpretation findings and diagnosis name of the medical image displayed on the monitor by using a mouse and a keyboard. Note that this processing is implemented by making the case information input terminal 200 have a function which allows selection by a GUI using, for example, an interpretation finding input support method based on a template form. In response to a request from the user, the case information input terminal 200 transmits already input information and expected diagnosis name which are associated with the abnormal shadow of the lung, and accompanying data (e.g., typical images) to the medical diagnosis support apparatus 100 via a LAN or the like.

The medical diagnosis support apparatus 100 is constituted by the constituent elements to be described below.

A medical information acquisition unit 102 acquires the already input information associated with the abnormal shadow of the lung and the accompanying data which are input from the case information input terminal 200 to the medical diagnosis support apparatus 100, and outputs the acquired data to a support information candidate acquisition unit 106, an inference unit 108, and a presentation unit 116.

An expected diagnosis name acquisition unit 104 acquires, as an expected diagnosis name, the diagnosis name expected by the doctor concerning the abnormal shadow of the lung which is input from the case information input terminal 200 to the medical diagnosis support apparatus 100, and outputs the diagnosis name to an influence acquisition unit 112 and the presentation unit 116.

The support information candidate acquisition unit 106 acquires (selects) at least one set of medical information determined based on already input information as a support information candidate. The acquired support information candidate is output to the inference unit 108 and the influence acquisition unit 112.

The inference unit 108 executes inference based on the already input information acquired by the medical information acquisition unit 102 which is associated with the abnormal shadow of the lung as a diagnosis target, and calculates the probability (already input information inference result) of the abnormal shadow being each diagnosis name. The inference unit 108 also executes inference based on each support information candidate acquired by the support information candidate acquisition unit 106, and acquires the execution result (support information candidate inference result). The acquired already input information inference result is output to a comparative diagnosis name acquisition unit 110 and the presentation unit 116. Each support information candidate inference result is output to the influence acquisition unit 112.

The comparative diagnosis name acquisition unit 110 estimates a diagnosis name (inferred diagnosis name) by inference on the abnormal shadow using the already input information inference result acquired by the inference unit 108. The comparative diagnosis name acquisition unit 110 then acquires the acquired inferred diagnosis name as a comparative diagnosis name. The acquired comparative diagnosis name is output to the influence acquisition unit 112 and the presentation unit 116.

The influence acquisition unit 112 acquires the influence (first influence) of each support information candidate on the expected diagnosis name and the influence (second influence) of each support information candidate on the comparative diagnosis name. The influence acquisition unit 112 acquires these influences based on the support information candidate inference results acquired by the inference unit 108. The acquired influences are output to a selection unit 114.

The selection unit 114 selects support information to be presented based on the influence (first influence) of each support information candidate on the expected diagnosis name and the influence (second influence) of each support information candidate on the comparative diagnosis name which are acquired by the influence acquisition unit 112. The selected support information is output to the presentation unit 116.

The presentation unit 116 generates and displays information to be presented based on the already input information acquired by the medical information acquisition unit 102 and the expected diagnosis name acquired by the expected diagnosis name acquisition unit 104. The presentation unit 116 further generates and displays information to be presented based on the already input information inference result acquired by the inference unit 108, the comparative diagnosis name acquired by the comparative diagnosis name acquisition unit 110, and the support information acquired by the selection unit 114.

Note that at least some of the units of the medical diagnosis support apparatus 100 shown in FIG. 1 may be implemented as independent devices. Alternatively, each unit may be implemented as software which implements each function. Assume that in this embodiment, each unit is implemented by software.

Figure 2:
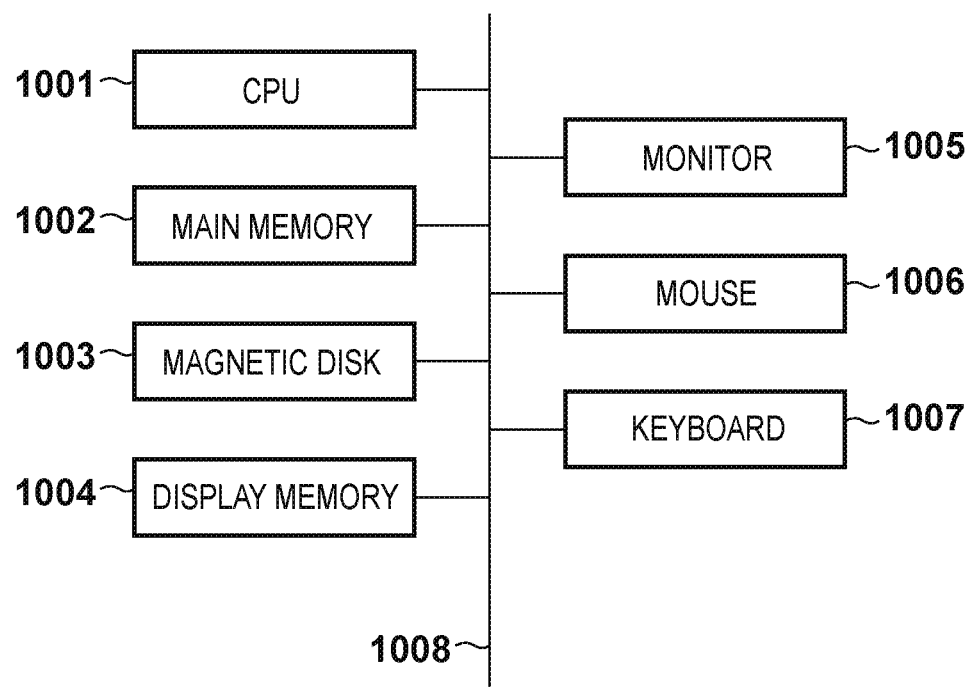
FIG. 2 is a block diagram showing the basic arrangement of a computer which implements each unit of the medical diagnosis support apparatus by using software.

FIG. 2 shows the basic arrangement of a computer for implementing the function of each unit shown in FIG. 1 by executing software. A CPU 1001 mainly controls the operation of each constituent element. A main memory 1002 stores control programs to be executed by the CPU 1001, and provides a work area at the time of execution of a program by the CPU 1001. A magnetic disk 1003 stores an OS (Operating System), device drives for peripheral devices, various kinds of application software including programs for processing to be described later, and the like. A display memory 1004 temporarily stores the display data generated by the presentation unit 116. A monitor 1005 is, for example, a CRT monitor or liquid crystal monitor, and displays an image, text, and the like based on data from the display memory 1004. A mouse 1006 and a keyboard 1007 are used by the user to perform pointing input and input characters and the like. The above constituent elements are communicatively connected to each other via a common bus 1008.

Figure 3:
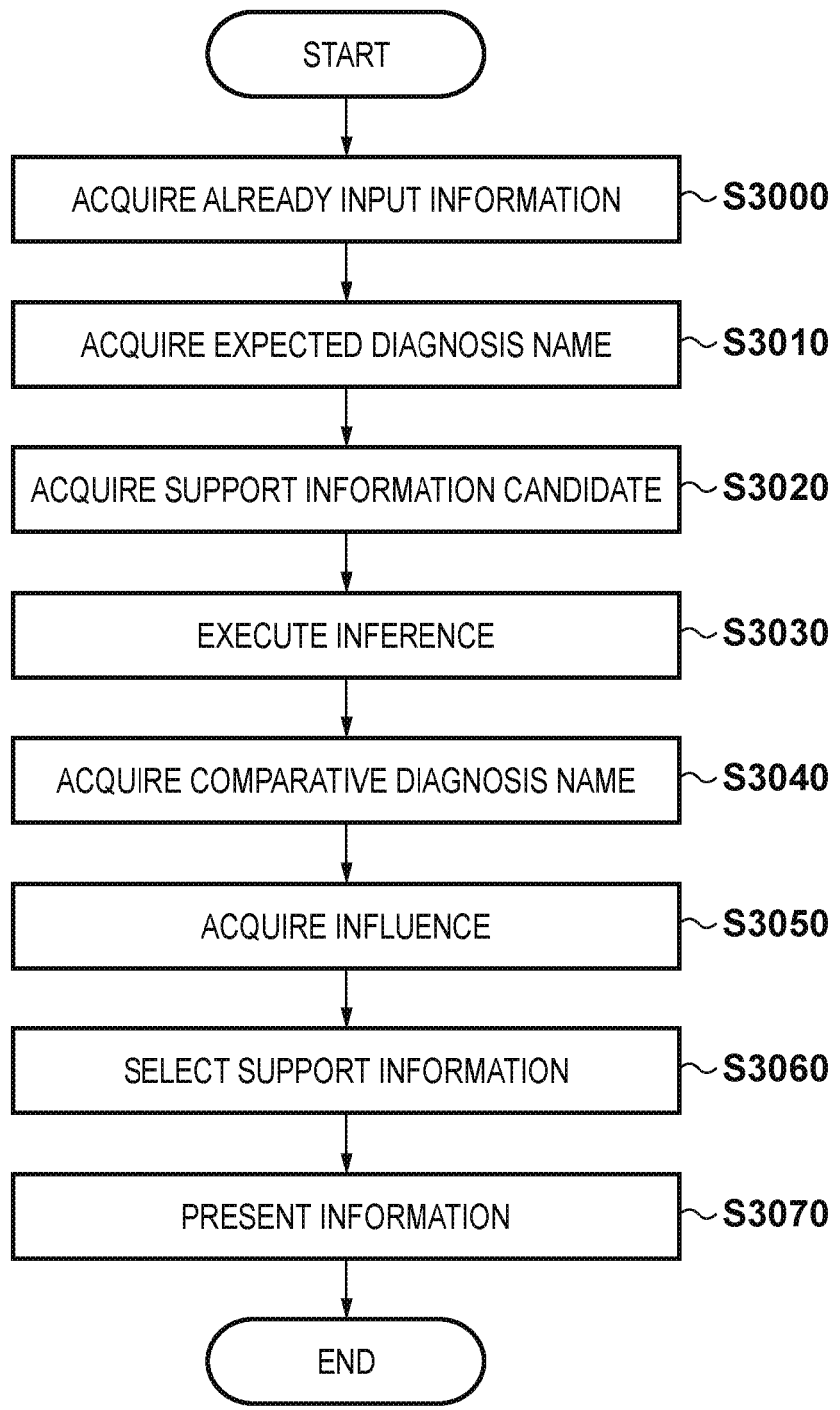
FIG. 3 is a flowchart showing an overall processing procedure in the first embodiment.

The overall processing performed by the medical diagnosis support apparatus 100 will be described next with reference to the flowchart of FIG. 3. In this embodiment, the CPU 1001 implements this processing by executing a program for implementing the function of each unit which is stored in the input information acquisition unit 1002.

In the following description, each interpretation finding item is represented by Ij (j=1 to n), and n types of interpretation findings I1 to In are handled. In addition, states (discrete values) which Ij can take are written as Sjk. The range of k varies in value depending on Ij. Assume that in this embodiment, it is possible to input interpretation findings like those shown in FIG. 7, and the respective interpretation findings can take states like those shown in FIG. 7.

For example, "shape" of I1 represents the shape of an abnormal shadow, and takes three states, namely S11 "sphere", S12 "lobulation", and S13 "irregular shape". "Lobation" of I2 represents the degree of lobation in an abnormal shadow. In addition, "engulfment (blood Vessel)" of In represents the presence/absence of the engulfment of a blood vessel in the abnormal shadow.

In the following description, a set of Ij and a set of Sjk are respectively written as N and E. Assume however that more than one state Sjk corresponding to a given interpretation finding Ij does not simultaneously exist in one E. For example, if I1 takes S11, S12, and S13, and I2 takes S21, S22, S23, and S24, E={S11, S21} holds, but E={S11, S12} does not hold. This is because one interpretation finding takes only one state.

In this case, a set of interpretation findings of already input information is written as NF, and a set of states of NF is written as Ef. In addition, a subset of Ef is written as Efl (l=1, 2, . . . ). Efl corresponds to a support information candidate. In the following description, a diagnosis name will be written as a symbol D. According to this embodiment, the diagnosis name has three values respectively representing primary lung cancer, lung cancer metastasis, and others, which are respectively written as D1, D2, and D3. In this case, the inference probability of a diagnosis name Dr (r=1, 2, 3) with no information being given will be written as P(Dr) (to be also referred to as the prior probability). In addition, the inference probability of the diagnosis name Dr with input information being given as E is written as P(Dr|E) (to be also referred as the posterior probability). In addition, this embodiment uses a diagnosis name (estimated diagnosis name) exhibiting a highest probability as a comparative diagnosis name, and an expected diagnosis name and an estimated diagnosis name are respectively written as Ddct and Dinf. Ddct and Dinf each take any one of D1, D2, and D3.

In addition, the influences of the support information candidate Efl on the expected diagnosis name Ddct and the estimated diagnosis name are respectively written as IR(Ddct|Efl) and IR(Dinf|Efl).

In step S3000, the medical diagnosis support apparatus 100 acquires already input information concerning an abnormal shadow of the lung input to the medical diagnosis support apparatus 100 and accompanying data. This operation is performed as processing by the medical information acquisition unit 102. Assume that the interpretation finding information which the medical diagnosis support apparatus 100 has acquired in step S3000 is I1 "shape": S11 "sphere", I3 "radial": S33 "weak", . . . , In "Engulfment (Blood Vessel)": Sn3 "none". In this case, the set Nf of interpretation findings of the already input information is given as Nf={I1, I3, . . . , In}, and the set Ef of the states of Nf is given as Ef={S11, S33, . . . , Sn3}.

In step S3010, the medical information acquisition unit 102 acquires, as an expected diagnosis name, the diagnosis name expected by the doctor concerning the abnormal shadow of the lung which is input to the medical diagnosis support apparatus 100. If, for example, the diagnosis name acquired by the medical diagnosis support apparatus 100 in step S3010 is D3 "others", the expected diagnosis name Ddct is expressed as Ddct=D3. In addition, if the input from doctor which is acquired by the medical diagnosis support apparatus 100 is information representing the degree of confidence of the doctor with respect to each diagnosis name, such as "possible", "suspected", or "strongly suspected", the apparatus selects a diagnosis name exhibiting a highest degree of confidence as an expected diagnosis name.

In step S3020, the support information candidate acquisition unit 106 acquires at least one of sets of medical information determined based on already input information as a support information candidate. In this embodiment, a subset (that is, Efl) of already input information selected based on a predetermined rule is used as a support information candidate. When, for example, using a rule that if the number of elements of the already input information Ef is 10, the number of elements included in Efl is limited to one, the support information candidate acquisition unit 106 acquires 10 support information candidates. When using a rule that the number of elements included in Efl is limited to one or two, the support information candidate acquisition unit 106 acquires 55 support information candidates obtained by adding 45 combinations of two candidates out of 10 candidates to the above 10 support information candidates.

In step S3030, the inference unit 108 infers the probability (already input information inference result) of the abnormal shadow of the lung being each diagnosis name based on the already input information (that is, Ef) of the abnormal shadow of the lung acquired in step S3000. In addition, the inference unit 108 infers the probability (support information candidate inference result) of the abnormal shadow being each diagnosis name based on only each support information candidate (Efl in this embodiment) acquired in step S3020.

As an inference technique at this time, it is possible to use one of various existing inference techniques such as a Bayesian network, neural network, and support vector machine. This embodiment uses a Bayesian network as an inference technique. The Bayesian network is an inference model using conditional probabilities. It is possible to obtain the inference probability (that is, posterior probability) of each diagnosis name when already input information is input. In this embodiment, the inference unit 108 acquires the probabilities of types D1, D2, and D3 of abnormal shadows.

In step S3040, the comparative diagnosis name acquisition unit 110 determines a comparative diagnosis name by using the already input information inference result acquired in step S3030. This embodiment uses a diagnosis name (estimated diagnosis name), of the types D1, D2, and D3 of abnormal shadows, which exhibits a highest probability as a comparative diagnosis name. If, for example, D1=25.2%, D2=42.5%, and D3=32.3%, the comparative diagnosis name (estimated diagnosis name) Dinf is expressed as Dinf=D2.

In step S3050, the influence acquisition unit 112 acquires the influence (first influence) of each support information candidate on the expected diagnosis name and the influence (second influence) of each support information candidate on the comparative diagnosis name. In this embodiment, the influence acquisition unit 112 calculates the influence IR(Ddct|Efl) of the support information candidate Efl on the expected diagnosis name Ddct, and the influence IR(Dinf|Efl) of the support information candidate Efl on the comparative diagnosis name (estimated diagnosis name), according to the following equations:

$$IR(D_{dct}|E_{fl})=P(D_{dct}|E_{fl})-P(D_{dct})$$

$$IR(D_{inf}|E_{fl})=P(D_{inf}|E_{fl})-P(D_{inf}) \quad (1)$$

That is, the difference between the prior probability of the diagnosis name and the posterior probability obtained when a diagnosis name is inferred by using the support information candidate Efl is defined as an influence. In this case, if the influence is positive, it is conceivable that the support information candidate Efl has increased the probability, whereas if the influence is negative, it is conceivable that the support information candidate Efl has decreased the probability. In this embodiment, if this influence is positive, the corresponding information is referred to as positive information, whereas if the influence is negative, the corresponding information will be referred to as negative information. Note that it is possible to hold in advance a correspondence table obtained in advance by calculating the influences of all possible support information candidates based on equations (1) and acquire influences from the correspondence table in the processing in step S3050.

In step S3060, the selection unit 114 selects support information to be presented based on the influence (first influence) of each support information candidate on the expected diagnosis name and the influence (second influence) of each support information candidate on the comparative diagnosis name, which are acquired in step S3050. For example, the selection unit 114 selects only a negative support information candidate with respect to the expected diagnosis name as support information. Alternatively, the selection unit 114 selects a support information candidate which is positive for one of the expected diagnosis name and the comparative diagnosis name and negative for the other diagnosis name. Obviously, the selection unit 114 may use other methods. In this embodiment, the selection unit 114 selects information from the support information candidates Efl whose influences IR(Ddct|Efl) on the expected diagnosis name are negative and influences IR(Dinf|Efl) on the comparative diagnosis name are positive. In addition, the selection unit 114 selects a support information candidate exhibiting a highest influence IR(Dinf|El) among such support information candidates as support information to be presented. That is, the selection unit 114 selects a support information candidate exhibiting a highest affirmation degree concerning the comparative diagnosis name among the support information candidates positive for the comparative diagnosis name and negative for the expected diagnosis name.

In step S3070, the presentation unit 116 displays the following information on the monitor 1005:
  the information (the already input information and representative image) concerning the abnormal shadow of the lung which is obtained in step S3000,
  the expected diagnosis name obtained in step S3010,
  the already input information inference result acquired in step S3030,
  the comparative diagnosis name obtained in step S3040, and
  the support information obtained in step S3060.

Figure 4:
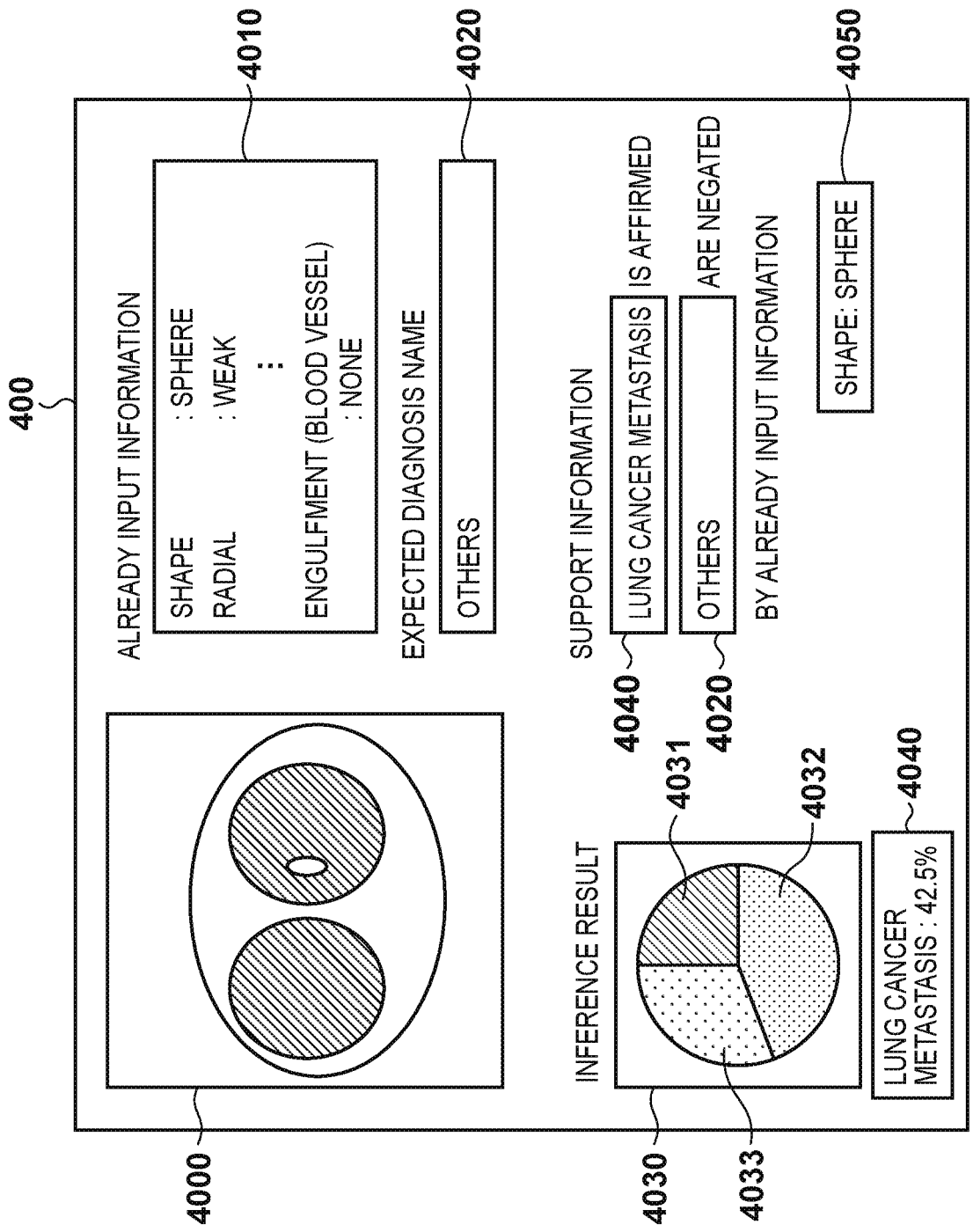
FIG. 4 is a view showing an example of support information in the first embodiment.

FIG. 4 shows an example of presentation information to be displayed on the monitor 1005 in this embodiment. Presentation information 400 includes a representative image 4000 of the abnormal shadow of the lung, already input information 4010 of the abnormal shadow of the lung acquired in step S3000, and an expected diagnosis name 4020 acquired in step S3010. The presentation information 400 also includes already input information inference result 4030 acquired in step S3030 and a comparative diagnosis name (estimated diagnosis name) 4040 acquired in step S3040. In the example shown in FIG. 4, the apparatus displays in a pie chart, as the already input information inference result 4030, an inference probability 4031 of a primary lung cancer in the already input information inference result, an inference probability 4032 of a lung cancer metastasis, and an inference probability 4033 of others. In addition, the presentation information 400 includes support information 4050 acquired in step S3060.

If the expected diagnosis name matches the comparative diagnosis name, it is possible to select and display only positive information for the matched diagnosis name as support information. Alternatively, it is possible to display both positive information and negative information. In this case, a display control can be performed so as to display the positive information and the negative information in different display forms. Furthermore, no support information may be displayed.

According to this embodiment, the doctor can refer to both the inference result (comparative diagnosis name) presented by the diagnosis support apparatus and information which is negative for the diagnosis name (expected diagnosis name) expected by the doctor himself/herself and positive for the estimated diagnosis name as support information. If, therefore, an expected diagnosis name differs from a comparative diagnosis name, in particular, the doctor can efficiently check information indicating why the diagnosis support apparatus has made such an estimation, which is necessary for the doctor to make final determination.

(First Modification of First Embodiment)

In the above embodiment, in step S3040, the apparatus acquires a diagnosis name (estimated diagnosis name) exhibiting a highest inference probability as a comparative diagnosis name. However, the apparatus may acquire a comparative diagnosis name by other methods. For example, the apparatus may acquire a diagnosis name having a higher importance than an expected diagnosis name as a comparative diagnosis name. In this case, assume that a predetermined importance Qr is defined in advance concerning each diagnosis name Dr. In step S3040, the apparatus acquires, as a comparative diagnosis name, a diagnosis name having an importance higher than an importance Qdoc of the expected diagnosis name (that is, satisfying Qdoc<Qr). For example, in the above case, if Q1=0.9, Q2=0.5, and Q3=0.1 and D2 "lung cancer metastasis" is acquired as an expected diagnosis name, the apparatus acquires D1 "primary lung cancer" as a comparative diagnosis name. If there are a plurality of diagnosis names having higher importances than the expected diagnosis name, one of the diagnosis names which exhibits a highest inference probability can be acquired as a comparative diagnosis name. Alternatively, the apparatus may acquire all diagnosis names, of the inference results, which exhibit high possibilities (inference probabilities higher than a predetermined threshold). Alternatively, the apparatus may acquire a diagnosis name having the highest importance as a comparative diagnosis name.

This will present already input information which is positive for a diagnosis name having a higher importance than the expected diagnosis name expected by the doctor and negative for the expected diagnosis name expected by the doctor. Referring this information allows the doctor to perform diagnosis in consideration of the possibility of the diagnosis name having a high importance.

(Second Modification of First Embodiment)

In the above embodiment, in step S3060, the apparatus selects only one support information candidate as support information. However, the apparatus may select a plurality of support information candidates as support information. For example, the apparatus may select, as support information, all support information candidates, of support information candidates satisfying conditions, which exhibit influences higher than a predetermined threshold. Alternatively, the apparatus may select all support information candidates satisfying conditions as support information. This makes it possible to present support information exhibiting high influences to the user without any omission.

(Third Modification of First Embodiment)

In the above embodiment, in step S3000, the doctor interprets the medical image displayed by the medical diagnosis support apparatus 100, and the apparatus acquires the interpretation findings as input information. However, the type of input information and a method of acquiring input information are not limited to them. For example, it is possible to use, as target input information (already input information/non-input information), past interpretation reports and medical charts concerning an object and an image analysis result on a medical image. In addition, it is possible to use, as target input information, medical examination data including other kinds of information which can be used for diagnosis support processing.

[Second Embodiment]

A medical diagnosis support apparatus according to the second embodiment selects and presents, as a support information candidate, medical information (non-input information), other than already input information, which can be input.

Note that the arrangement of the medical diagnosis support apparatus according to this embodiment is the same as that shown in FIG. 1 in the first embodiment. However, the second embodiment differs from the first embodiment in that a support information candidate to be acquired by a support information candidate acquisition unit 106 is selected from non-input information other than already input information. The second embodiment also differs from the first embodiment in that an inference unit 108 acquires a support information candidate inference result based on already input information and a support information candidate. In addition, the second embodiment differs from the first embodiment in that an influence acquisition unit 112 performs influence acquisition processing based on the already input information inference result and support information candidate inference result acquired by the inference unit 108.

The basic arrangement of a computer which implements a medical diagnosis support apparatus 100 by executing software is the same as that shown in FIG. 2 in the first embodiment. A flowchart for explaining the overall processing performed by the medical diagnosis support apparatus 100 is the same as that shown in FIG. 3. However, the processing performed in steps S3020, S3030, S3050, and S3060 partly differs from that in the first embodiment. Only portions of the overall processing performed by the medical diagnosis support apparatus 100 according to this embodiment which differ from that performed by the first embodiment will be described below with reference to the flowchart of FIG. 3.

In this case, a set of interpretation findings corresponding to information Nf other than already input information is written as ¬Nf, and a set of states in ¬Nf which can be combined as elements is written as Evm (m=1, 2, ... ). Evm corresponds to support information candidates in this embodiment. In addition, the influence of the support information candidate Evm on an expected diagnosis name Ddct and an estimated diagnosis name Dinf are respectively written as IR(Ddct|Evm) and IR(Dinf|Evm).

Each of the processes in steps S3000 and S3010 is the same as that in the first embodiment.

In step S3020, the support information candidate acquisition unit 106 acquires at least one set of medical information determined based on already input information as a support information candidate. In this embodiment, unlike in the processing in the first embodiment, the support information candidate acquisition unit 106 acquires, as a support information candidate, a set (that is, Evm) generated from non-input information as medication information other than already input information. Consider, for example, a case in which ¬Nf={I2, I6, I8}, I2 takes S21, S22, S23, and S24, I6 takes S61 and S62, and I8 takes S81, S82, and S83. If, for example, the number of elements to be included in Evm is limited to one, the support information candidate acquisition unit 106 acquires 4+2+3=9 support information candidates. Alternatively, if the number of elements to be included is limited to 1 or 2, the support information candidate acquisition unit 106 acquires 9+4×2+4×3+2×3=35 support information candidates.

In step S3030, the inference unit 108 acquires an already input information inference result based on already input information by performing the same processing as that in step S3030 in the first embodiment. In addition, unlike the processing in the first embodiment, the inference unit 108 infers, as a support information candidate inference result, the probability of the abnormal shadow being each diagnosis name based on a pair of already input information and a support information candidate (Evm in this embodiment). Note that it is possible to execute this inference by the same inference processing as that in the first embodiment.

The processing in step S3040 is the same as that in the first embodiment. That is, an estimated diagnosis name is used as a comparative diagnosis name.

In step S3050, the influence acquisition unit 112 acquires the influence (first influence) of each support information candidate on the expected diagnosis name and the influence (second influence) of each support information candidate on the comparative diagnosis name. In this embodiment, the influence acquisition unit 112 calculates the influence IR(Ddct|Evm) of the support information candidate Evm on the expected diagnosis name Ddct, and the influence IR(Dinf|Evm) of the support information candidate Evm on the estimated diagnosis name Dinf, according to the following equations:

$$IR(D_{dct}|E_{vm}) = P(D_{dct}|E_{vm}\blacksquare E_f) - P(D_{dct}|E_f)$$

$$IR(D_{inf}|E_{vm}) = P(D_{inf}|E_{vm}\blacksquare E_f) - P(D_{inf}|E_f) \quad (2)$$

That is, the influence of the support information candidate Evm is the degree to which the inference result of a target diagnosis name is made to vary by adding Evm to already input information. That is, if the influence is positive, the addition of Evm increases the inference probability, whereas if the influence is negative, the addition of Evm decreases the inference probability. In this embodiment, like the first embodiment, if this influence is positive, the corresponding information is referred to as positive information, whereas if the influence is negative, the corresponding information will be referred to as negative information.

In step S3060, a selection unit 114 selects support information to be presented, based on the influence of each support information candidate on the expected diagnosis name and the influence of each support information candidate on the comparative diagnosis name, which are acquired in step S3050. For example, the selection unit 114 selects only a positive support information candidate for the expected diagnosis name as support information. Alternatively, the selection unit 114 selects a support information candidate which is positive for one of the expected diagnosis name and the comparative diagnosis name and negative for the other diagnosis name. Obviously, the selection unit 114 may use other methods. In this embodiment, the selection unit 114 selects information from the support information candidates Evm whose influence IR(Ddct|Evm) on the expected diagnosis name is positive and influence IR(Dinf|Evm) on the comparative diagnosis name is negative. In addition, the selection unit 114 selects one of such support information candidates which has the highest influence IR(Ddct|Evm). That is, the selection unit 114 selects a support information candidate, of the support information candidates positive for the expected diagnosis name and negative for the comparative diagnosis name, which exhibits a highest affirmation degree concerning the expected diagnosis name.

The processing in step S3070 is the same as that in the first embodiment.

Figure 5:
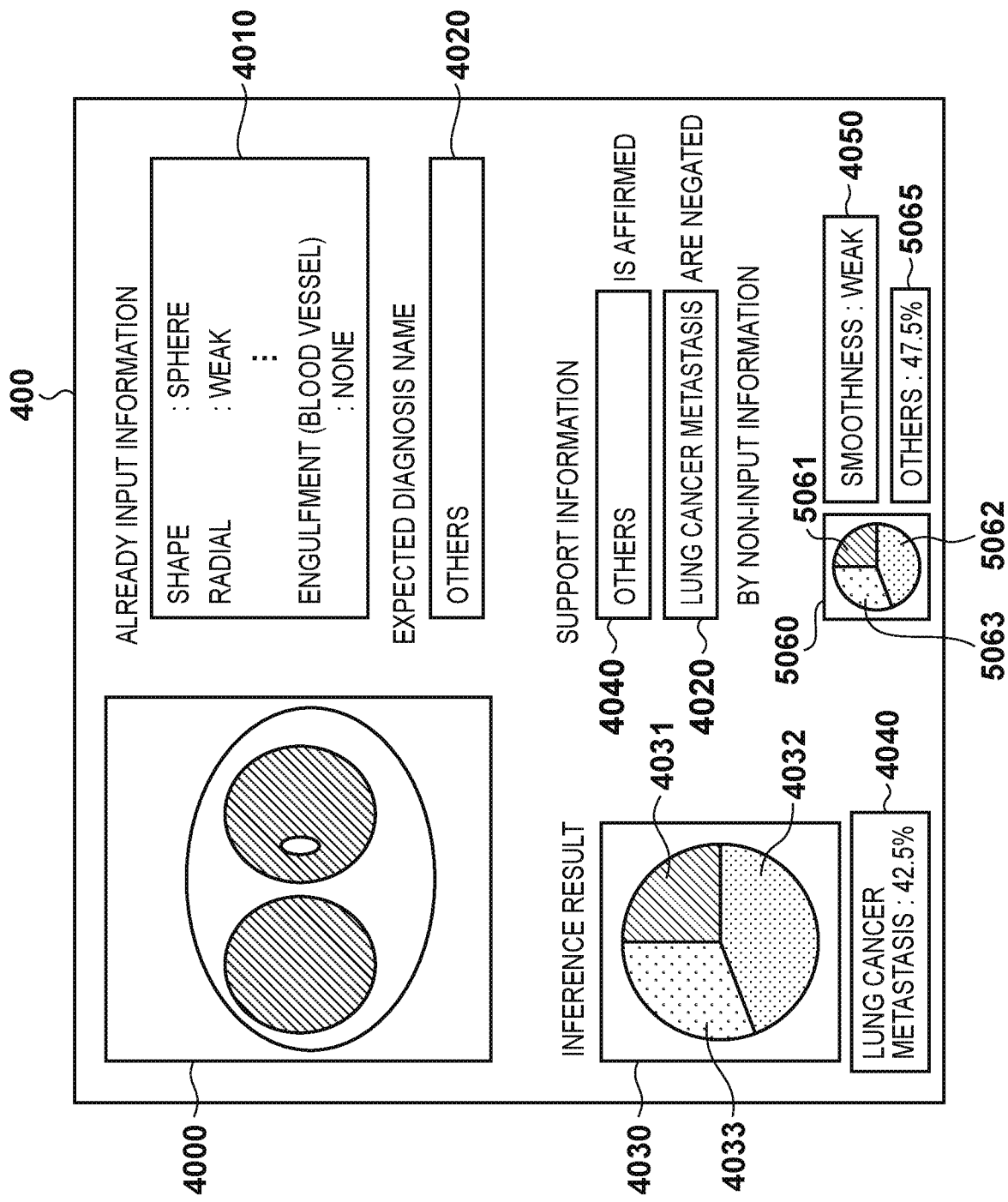
FIG. 5 is a view showing an example of support information in the second embodiment.

FIG. 5 shows an example of the presentation information displayed on a monitor 1005 in this embodiment. In the example shown in FIG. 5, the presentation information includes a support information candidate inference result 5060 when support information 4050 is added to the example in FIG. 4. In the example shown in FIG. 5, the support information candidate inference result 5060 includes an inference probability 5061 of a primary lung cancer in the already input information inference result, an inference probability 5062 of a lung cancer metastasis, and an inference probability 5063 of others, which are displayed in a in a pie chart, and a diagnosis name 5065 obtained when support information is input.

According to this embodiment, the doctor can refer to both the inference result (comparative diagnosis name) presented by the diagnosis support apparatus and information which is positive for the diagnosis name (expected diagnosis name) expected by the doctor himself/herself and negative for the comparative diagnosis name as support information. That is, when the doctor inputs a value, he/she can refer to information which makes an inference result recede from the comparative diagnosis name and approach the expected diagnosis name. It is therefore possible to efficiently determine whether the diagnosis name expected by the doctor is correct by checking whether there is presented support information in an image.

(First Modification of Second Embodiment)

In the second embodiment described above, in step S3060, the selection unit 114 selects, as support information to be presented, a support information candidate, of support information candidates whose influences on an expected diagnosis name are positive and influences on a comparative diagnosis name are negative, which exhibits a highest influence on the expected diagnosis name. However, other selection conditions may be used. For example, the selection unit 114 may select only support information which makes an estimated diagnosis name match the diagnosis name (second comparative diagnosis name) acquired from a support information candidate inference result (second inference result) when support information is input. That is, the selection unit 114 may select support information which changes an estimated diagnosis name to an expected diagnosis name as it is input. In this case, since an estimated diagnosis name changes to an expected diagnosis name, it is possible to further efficiently determine whether the diagnosis name expected by the doctor is correct by checking support information.

(Other Modifications of Second Embodiment)

The modifications described in the first embodiment can be applied to the second embodiment.

[Third Embodiment]

A medical diagnosis support apparatus according to the third embodiment uses non-input information as a support information candidate and presents the fluctuation of an inference result when the non-input information is input.

Note that the arrangement of the medical diagnosis support apparatus according to this embodiment is the same as that shown in FIG. 1 in the second embodiment. In addition, the basic arrangement of a computer which implements a medical diagnosis support apparatus 100 by executing software is the same as that shown in FIG. 2 in the second embodiment. A flowchart for explaining the overall processing performed by the medical diagnosis support apparatus 100 is the same as that shown in FIG. 3. However, the processing performed in steps S3020, S3060, and S3070 partly differs from that in the second embodiment. Only portions of the overall processing performed by the medical diagnosis support apparatus 100 according to this embodiment which differ from that performed by the second embodiment will be described below with reference to the flowchart of FIG. 3.

The processing in steps S3000 and S3010 is the same as that in the second embodiment.

In step S3020, a support information candidate acquisition unit 106 acquires at least one set of medical information determined based on already input information as a support information candidate. In this embodiment, unlike in the processing in the second embodiment, the support information candidate acquisition unit 106 acquires all the sets which can be generated from non-input information (that is, ¬Nf) as support information candidates. Consider, for example, a case in which ¬Nf={I2, I6, I8}, I2 takes S21, S22, S23, and S24, I6 takes S61 and S62, and I8 takes S81, S82, and S83. In this case, the support information candidate acquisition unit 106 acquires 9+{4×2+4×3+2×3}+4×2×3=59 support information candidates as all the sets which can be generated.

Each of the processes in steps S3030 to S3050 is the same as that in the second embodiment.

In step S3060, a selection unit 114 selects support information to be presented based on the influences of each support information candidate on the expected diagnosis name and the comparative diagnosis name which are acquired in step S3050. For example, the selection unit 114 selects only a support information candidate positive for the comparative diagnosis name as support information. Alternatively, the selection unit 114 selects a support information candidate which is positive for one of the expected diagnosis name and the comparative diagnosis name and negative for the other diagnosis name. Obviously, the selection unit 114 may use other methods. In this embodiment, the selection unit 114 selects information from support information candidates Evm whose influences IR(Ddct|Evm) on the expected diagnosis name are positive and influences IR(Dinf|Evm) on the comparative diagnosis name are negative. In addition, the selection unit 114 selects a support information candidate exhibiting a highest influence IR(Ddct|Evm) as support information (maximum positive information) to be presented. Furthermore, the selection unit 114 selects information from the support information candidates Evm whose influences IR(Ddct|Evm) on the expected diagnosis name are negative and influences IR(Dinf|Evm) on the comparative diagnosis name are positive. Moreover, the selection unit 114 selects a support information candidate exhibiting a lowest influence IR(Ddct|Evm) as support information to be presented (maximum negative information). That is, the selection unit 114 selects a support information candidate exhibiting a highest affirmation degree concerning the expected diagnosis name among the support information candidates positive for the expected diagnosis name and negative for the comparative diagnosis name. The selection unit 114 also selects a support information candidate exhibiting a highest negation degree concerning the expected diagnosis name among the support information candidates negative for the expected diagnosis name and positive for the comparative diagnosis name.

In step S3070, a presentation unit 116 presents the fluctuation of an inference result when the apparatus inputs maximum positive information and maximum negative information selected in step S3060 in addition to performing the processing in the second embodiment.

Figure 6:
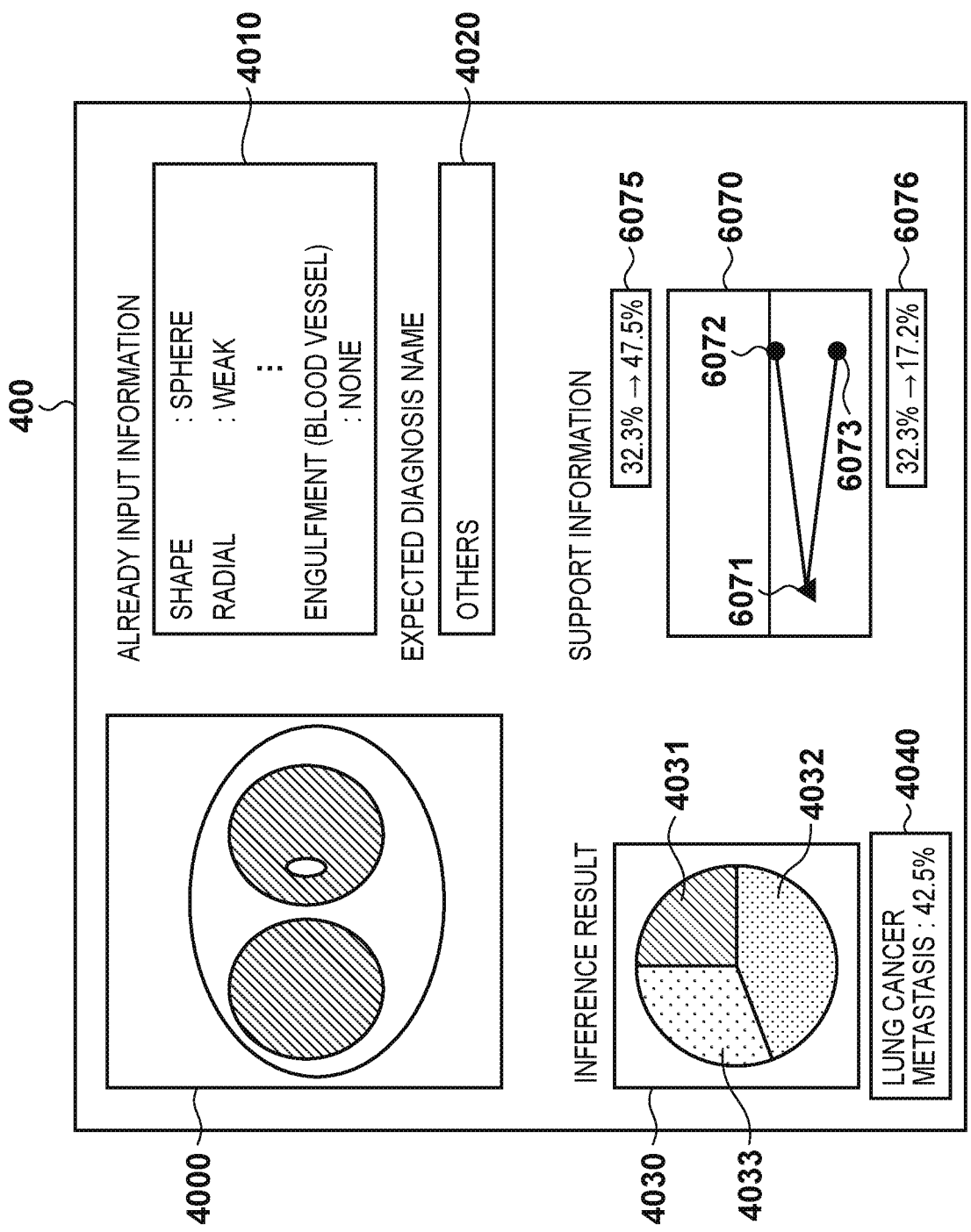
FIG. 6 is a view showing an example of support information in the third embodiment.

FIG. 6 shows an example of the presentation information displayed on a monitor 1005 in this embodiment. The example shown in FIG. 6 includes a support information candidate inference result fluctuation 6070 obtained by adding maximum positive information and maximum negative information to the example shown in FIG. 5. In the example shown in FIG. 6, the support information candidate inference result fluctuation 6070 includes another inference probability marker 6071 in already input information inference result. The support information candidate inference result fluctuation 6070 further includes another inference probability marker 6072 obtained when the maximum positive information is input and another inference probability marker 6073 obtained when the maximum negative information is input. In addition, this example includes another inference probability 6075 obtained when the maximum positive information is input and another inference probability 6076 obtained when the maximum negative information is input.

According to this embodiment, the doctor can refer to, as support information, an inference result (comparative diagnosis name) presented by diagnosis support processing and information indicating how the inference probability of the diagnosis name (expected diagnosis name) expected by the doctor by himself/herself varies when consideration is given to all possible non-input information. In other words, it is possible to refer to information indicating how stable the current inference result is. It is therefore possible to efficiently determine whether the inference result based on already input information is correct.

(First Modification of Third Embodiment)

In the third embodiment described above, in step S3020, the support information candidate acquisition unit 106 acquires all sets which can be generated from non-input information (that is, ¬Nf) as support information candidates. However, it is not always necessary to set all the sets which can be generated as support information candidates. For example, the number of elements included in support information candidates may be limited. In this case, if, for example, the number of elements is limited to five, it is possible to consider the variation of an inference result when the five maximum pieces of information are added to the already input information. In addition, the number of elements included in support information candidates may be increased stepwise. In this case, first of all, the number of elements included in support information candidates is limited to one, and support information candidates are acquired. The apparatus then performs the processing in steps S3030 to S3060 to acquire maximum positive information and maximum negative information. The process returns to step S3020 to acquire maximum positive support information candidates by adding the respective elements of non-input information which have not been selected to maximum positive information. Likewise, the apparatus acquires maximum negative information candidates by adding the respective elements of non-input information which have not been selected to maximum negative information. The apparatus then repeats the processing in step S3030 to S3060. The apparatus repeats this processing until there is non-input information not selected in step S3020. With this processing, it is possible to consider a variation close to the variation of an inference result in consideration of all combinations while suppressing a calculation cost.

(Second Modification of Third Embodiment)

In the above embodiment, in step S3070, the apparatus presents the fluctuation of an inference result when the maximum positive information and maximum negative information selected in step S3060 are input. However, it is not always necessary to present the fluctuation. For example, the apparatus may display "stable" when the difference between the inference result obtained when maximum positive information is input and the inference result obtained when maximum negative information is input is smaller than a threshold. In addition, in such a case, it is not necessary to select maximum positive information and maximum negative information in step S3060.

(Other Modifications of Third Embodiment)

The modifications described in the first and second embodiments can also be applied to the third embodiment.

(Other Embodiments)

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-029835, filed Feb. 14, 2012, which is hereby incorporated by reference herein in its entirety.

The invention claimed is:

1. A diagnosis support apparatus which supports diagnosis comprising:
at least one processor and a memory operatively coupled to function as:
an acquisition unit configured to acquire information of interpretation findings obtained by medical image interpretation, and acquire a diagnosis name set by a user; and
a presentation unit configured to present, based on at least the interpretation findings, information which is positive for the diagnosis name set by the user and negative for an inference result different from the diagnosis name set by the user and information which is negative for the diagnosis name set by the user and positive for the inference result different from the diagnosis name set by the user.

2. The apparatus according to claim 1, wherein the presentation unit is configured to present from information, of the information configured to be input, which has been used for the inference.

3. The apparatus according to claim 1, wherein the presentation unit is configured to present from information, of the information configured to be input, which has not been used for the inference.

4. The apparatus according to claim 1, wherein the presentation unit is configured to display on a display unit the information positive for the diagnosis name presented by the presentation unit and the information negative for the diagnosis name on a display unit in different display forms.

* * * * *